(12) United States Patent
Liao

(10) Patent No.: US 6,752,782 B2
(45) Date of Patent: Jun. 22, 2004

(54) AUTOMATICALLY RETRACTABLE SAFETY SYRINGE

(76) Inventor: Chin-Fu Liao, P.O. Box No. 6-57, Chung-Ho, Taipei 235 (TW)

(*) Notice: Subject to any disclaimer, the term of this patent is extended or adjusted under 35 U.S.C. 154(b) by 181 days.

(21) Appl. No.: 10/108,448

(22) Filed: Mar. 29, 2002

(65) Prior Publication Data

US 2003/0187400 A1 Oct. 2, 2003

(51) Int. Cl.[7] .............................................. A61M 5/00
(52) U.S. Cl. ....................... 604/110; 604/192; 604/198; 604/218; 604/263; 604/240; 604/242
(58) Field of Search ............................. 604/110, 192, 604/198, 195, 187, 218, 220, 197, 263, 200, 264, 181, 240–243, 244; 128/919

(56) References Cited

U.S. PATENT DOCUMENTS

| | | | | |
|---|---|---|---|---|
| 5,242,400 A | * | 9/1993 | Blake et al. ................. | 604/110 |
| 5,250,037 A | * | 10/1993 | Bitdinger ..................... | 604/192 |
| 5,451,214 A | * | 9/1995 | Hajishoreh ................... | 604/235 |
| 5,505,694 A | * | 4/1996 | Hubbard et al. ............. | 604/512 |
| 5,591,138 A | * | 1/1997 | Vaillancourt ................. | 604/263 |
| 5,984,899 A | * | 11/1999 | D'Alessio et al. .......... | 604/198 |
| 6,086,568 A | * | 7/2000 | Caizza ........................ | 604/218 |
| 6,368,303 B1 | * | 4/2002 | Caizza ........................ | 604/110 |
| 6,409,701 B1 | * | 6/2002 | Cohn et al. ................. | 604/110 |
| 6,432,087 B1 | * | 8/2002 | Hoeck et al. ............... | 604/181 |
| 6,494,863 B1 | * | 12/2002 | Shaw et al. ................. | 604/110 |
| 6,558,357 B1 | * | 5/2003 | Hoeck ......................... | 604/195 |
| 2003/0149403 A1 | * | 8/2003 | Barker et al. ............... | 604/198 |

* cited by examiner

*Primary Examiner*—Brian L. Casler
*Assistant Examiner*—Cris L Rodriguez
(74) *Attorney, Agent, or Firm*—Troxell Law Office PLLC

(57) ABSTRACT

An automatically retractable safety syringe includes a needle assembly consisting of a cannula, a needle hub and a rubber O-ring, a needle cap, a retracting spring, a breakable and retractable plunger, a plunger gasket and a medicine barrel; in accordance with the structure of the said automatically retractable safety syringe of the present invention, since the breakable plunger is assembled inside the medicine barrel, after being pushed all the way to the end, it is forced to break automatically into two parts for reducing it's length so as to provide enough space for the retracting spring to drive the needle assembly moving along the sliding passages for accomplishing an automatically retracting action.

4 Claims, 7 Drawing Sheets

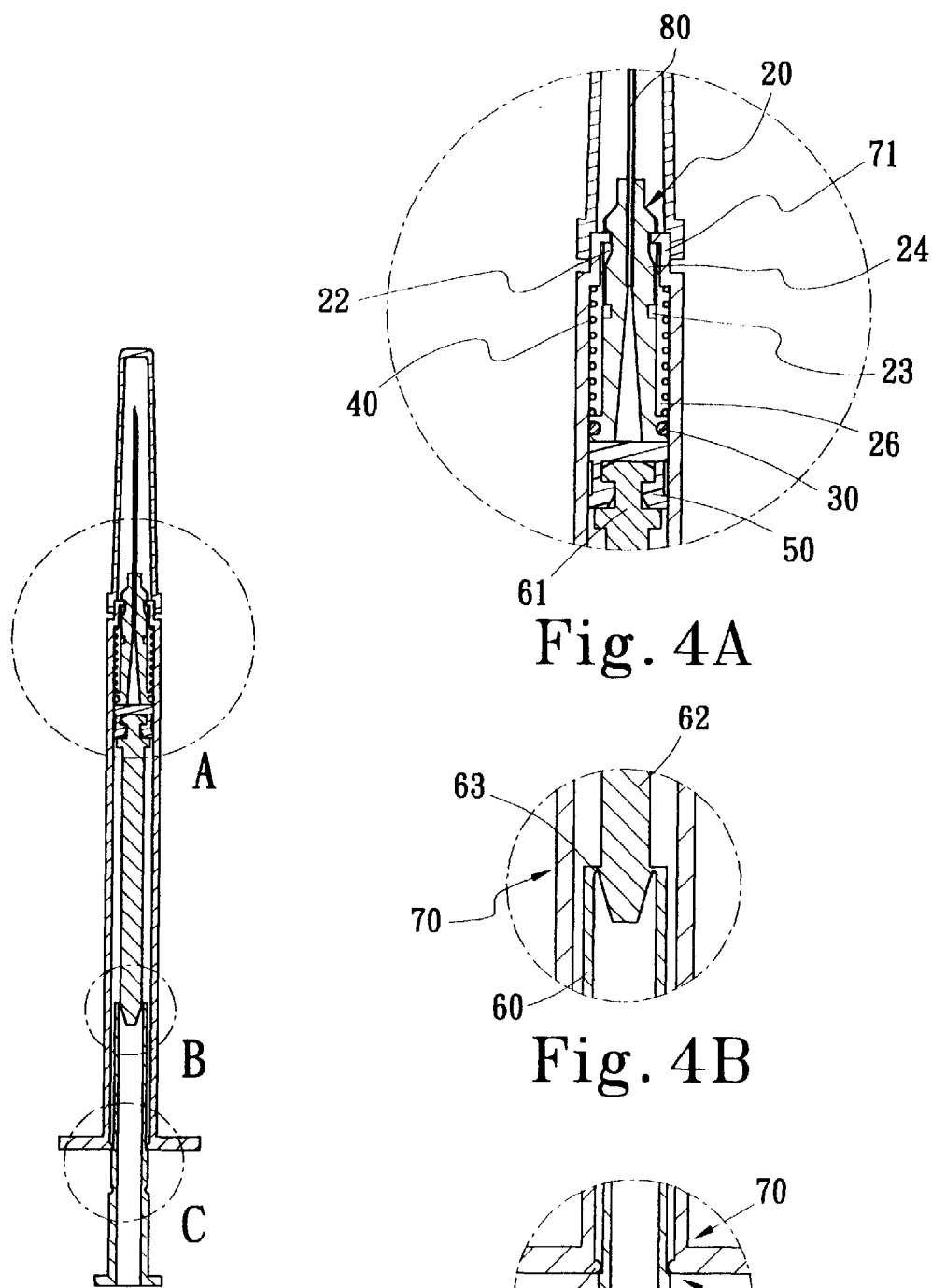
Fig. 4
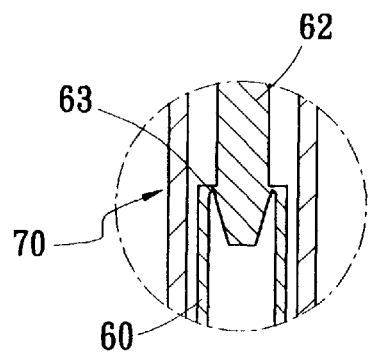
Fig. 4A
Fig. 4B
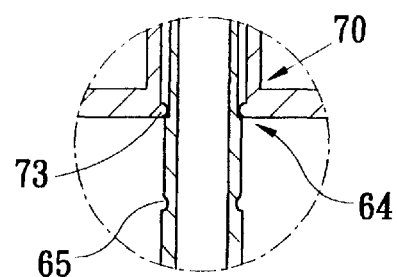
Fig. 4C

AUTOMATICALLY RETRACTABLE SAFETY SYRINGE

BACKGROUND OF THE INVENTION

1) Field of the Invention

The present invention relates to an automatically retractable safety syringe, more particularly to a syringe designed to be operated by single hand and to have an automatically retractable needle assembly not allowing for reuse.

2) Description of the Prior Art

Nowadays, since syringes have been widely used to inject medicine all around the world, needle sticking related injuries occur quite often; the sequelae caused by this kind of accident should not be overlooked because more than twenty kinds of diseases are infected through blood transmission, for example, HIV-1 (AIDS), Hepatitis B and C; it requires a considerable society cost for handling the follow-ups after injury accidents. The prior art safety syringe is usually operated manually by both hands; although the manufacturing cost thereof is low, its application is inconvenient and not safe enough either.

SUMMARY OF THE INVENTION

In view of the abovementioned needle stick injuries and shortcomings of the prior art safety syringe, the primary objective of the present invention is to provide a syringe designed to be operated by single hand, to have an automatically retractable needle assembly not allowing for reuse; the said automatically retractable safety syringe comprises a needle assembly with a cannula a needle hub and a rubber O-ring thereof, a needle cap, a retracting spring, a breakable plunger, a plunger rubber gasket and a medicine barrel; in accordance with the structure of the said automatically retractable safety syringe of the present invention, since the breakable plunger is assembled inside the medicine barrel, after being pushed all the way to the end, it is forced to break automatically into two parts for reducing it's length so as to provide enough space for the retracting spring to drive the needle assembly moving along the sliding passages to accomplish the automatically retracting action.

To enable a further understanding of the structural features and the technical contents of the present invention, the brief description of the drawings below is followed by the detailed description of the preferred embodiment.

BRIEF DESCRIPTION OF THE DRAWINGS

FIG. 4 is a lateral view and cross-sectional drawing of the present invention.

FIG. 4A is a partially enlarged drawing of the present invention.

FIG. 4B is another partially enlarged drawing of the present invention.

FIG. 4C is also another partially enlarged drawing of the present invention.

DETAILED DESCRIPTION OF THE PREFERRED EMBODIMENTS

Figure 1:
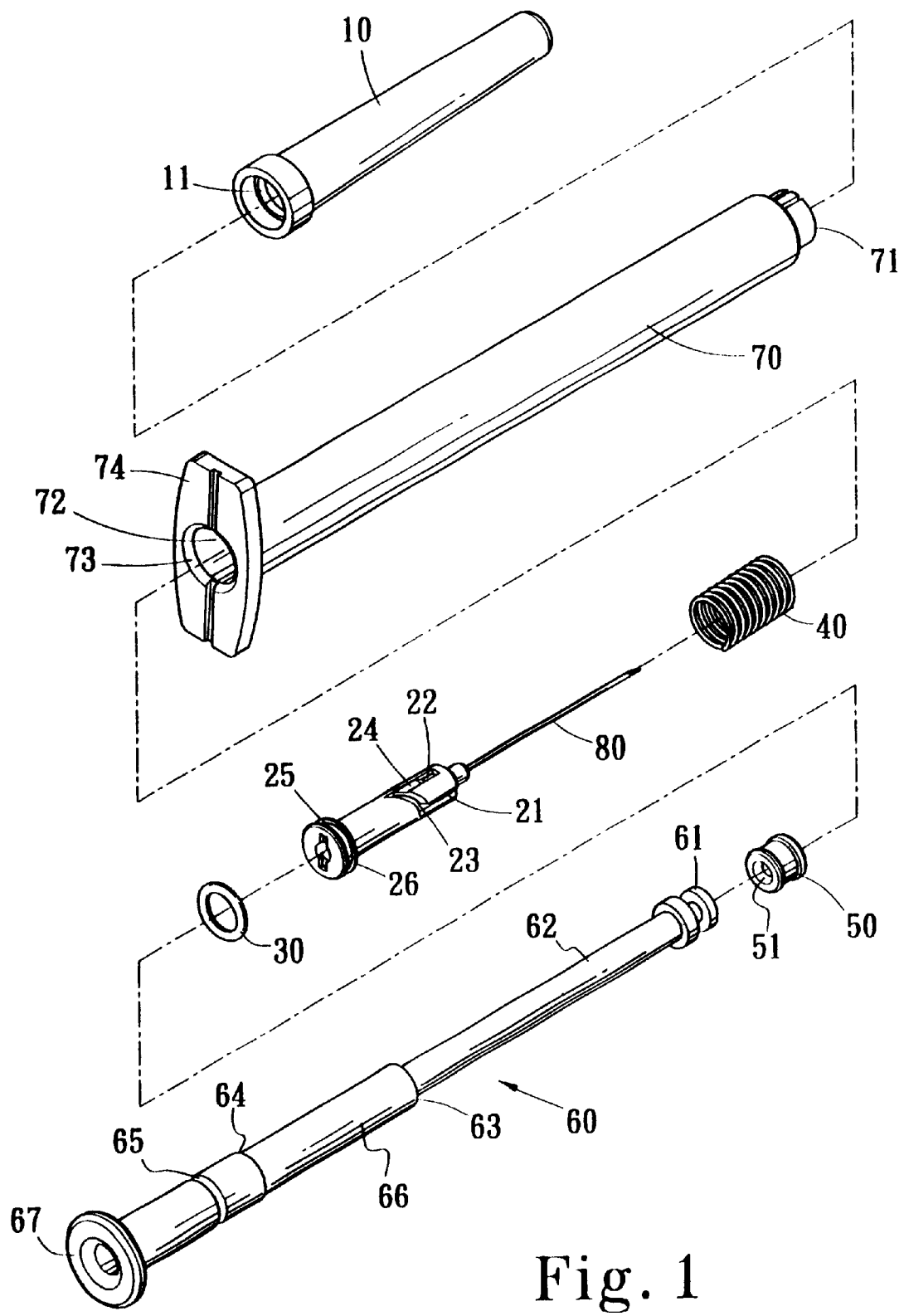
FIG. 1 is an exploded drawing of the present invention.
Figure 2:
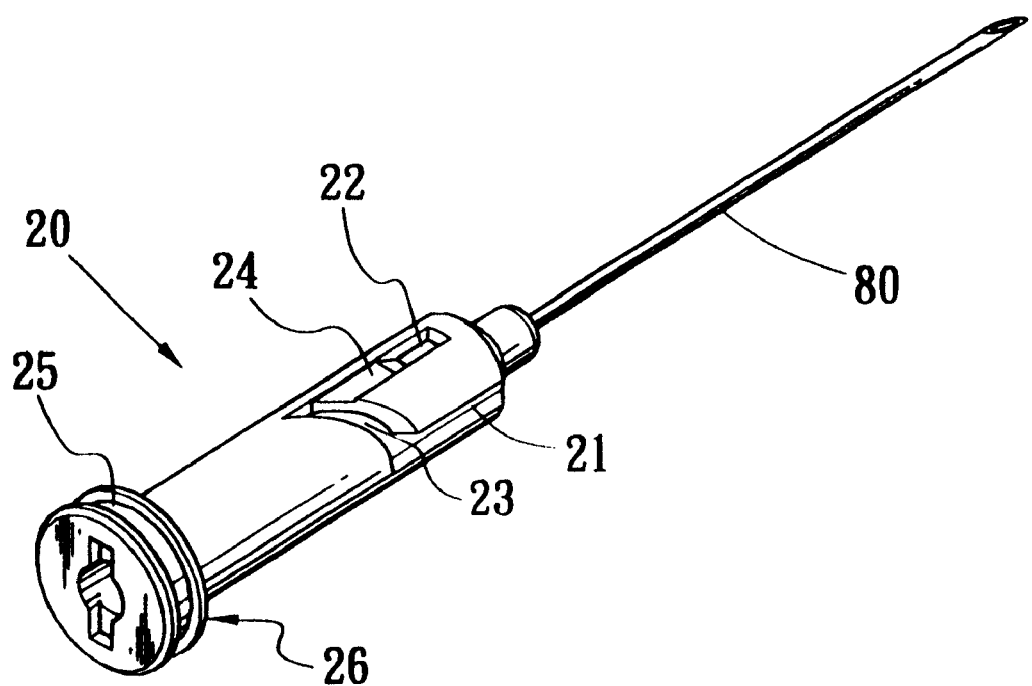
FIG. 2 is an enlarged drawing of a needle head of the present invention.
Figure 3:
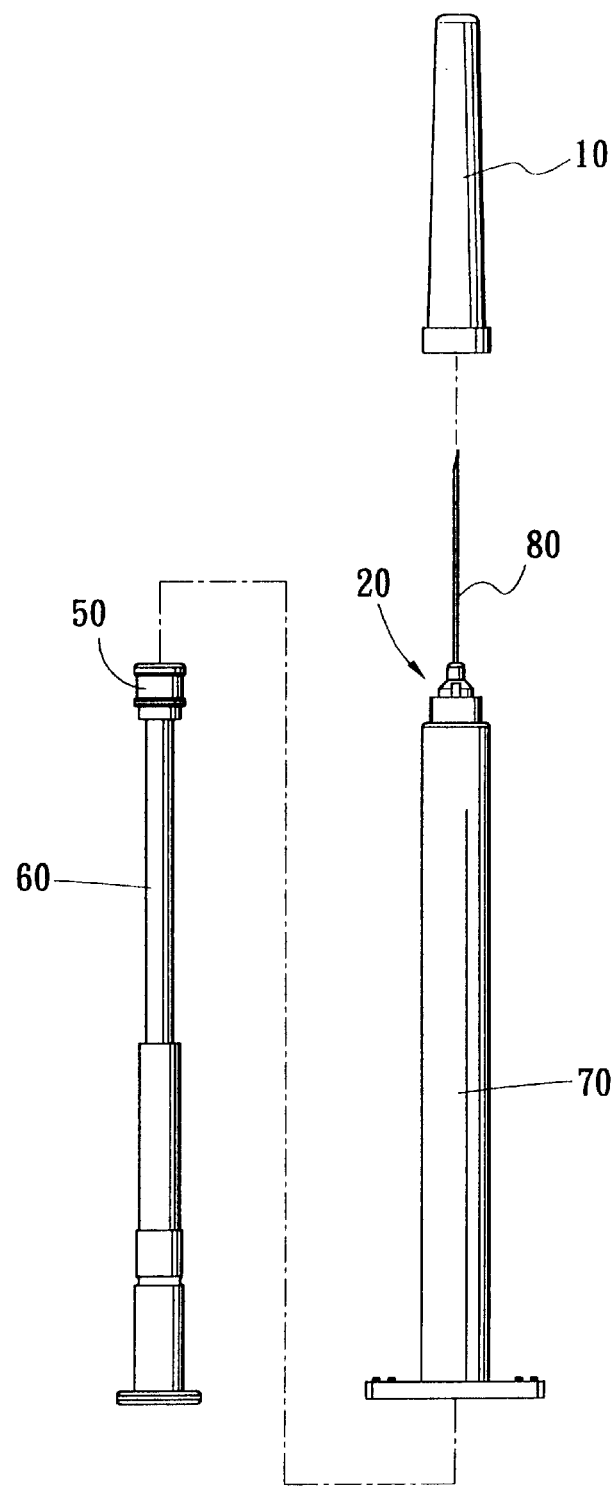
FIG. 3 is a lateral view and exploded drawing of the present invention.

As indicated in FIG. 1, the exploded drawings of the present invention, a needle assembly thereof has a cannula (80) and a needle hub (20) with one end thereof used for receiving the cannula (80) to fitly penetrate through its center; the circumference at the other end is disposed with an annular rubber gasket groove (25) and the convex torus thereof is disposed as a check plate (26) toward one end of an retracting spring (40); a plurality of concave positioning slots (22) are disposed in a proper area at two ends of the needle hub (20) to connect a plurality of proceeding slopes (24) tapered upwardly, a plurality of rotating slide passages (23) concaved inwardly and slanted for rotation as well as to connect a plurality of communicating slide passages (21) concaved inwardly to form an U-shaped slide passage for the needle assembly to make retracting action; a needle hub rubber gasket (30) is used for making a tight seal; an annular retracting spring (40) compresses and expands to retract the needle assembly; a plunger rubber gasket (50) is also used for making a tight seal; a breakable inwardly retracting plunger (60) is disposed with a long inwardly retracting rod (62) with one end disposed with a rubber clip head (61) to clip the plunger rubber gasket (50) and the other end thereof connected to one end of a hollow receiving rod (66) to form a breakable area (63) in an annular or annular block shape; the other end of the hollow receiving rod (66) is disposed with a push grip (67); an annular bottom check ring (64) is disposed in a proper area at the said two ends for controlling the bottom position of the syringe; an annular fastening annular groove (65) controls and fastens the breakable inwardly retracting plunger (60) to break into two parts and rotate with the needle assembly for completing inwardly retraction; the center of the hollow receiving rod (66) has a space for receiving the inwardly retracting rod (62); one end of a medicine barrel (70) is disposed with a plurality of slightly resilient retaining hook (71) pointing to the center for cooperating with the U-shape of the needle hub; the other end is disposed with a handle lug (74); the aperture of one end of a communicating inner barrel (72) is smaller than that of the inner barrel (72) to form a check ring for stopping the other end of the retracting spring (40); the other end of the said inner barrel (72) is disposed with an annular convex ring (73) for controlling and positioning the bottom check ring (64) and the fastening annular groove (65); the said inner barrel (72) has the space for receiving the needle assembly, the retracting spring (40), the breakable inwardly retracting plunger (60) and the plunger rubber gasket (50) thereof; a needle cap (10) covers to guard the needle assembly and fitly clips unto the retaining hook (71) of the medicine barrel (70); when the needle cap (10) is not separated from the retaining hook (71) of the medicine barrel (70), the retaining hook (71) does not eject for the needle assembly to retract.

Figure 5:
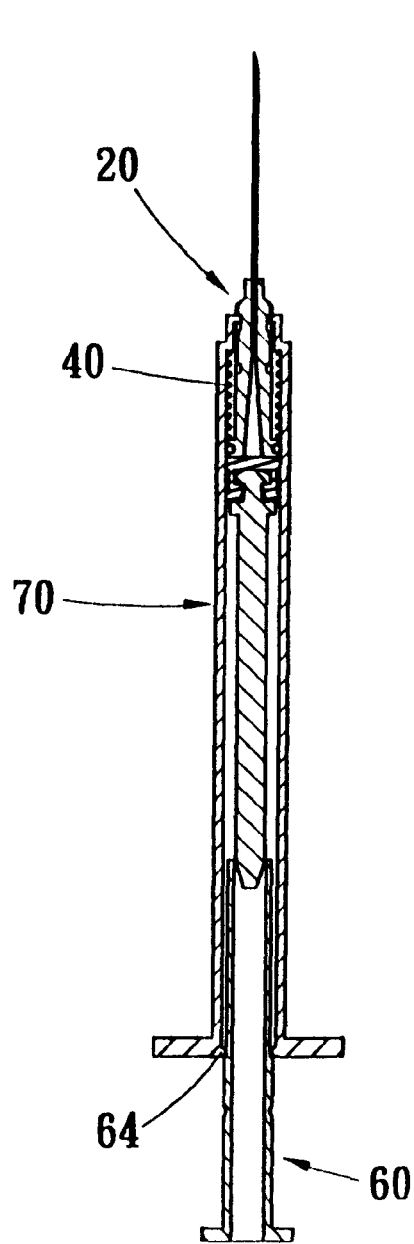
FIG. 5 is a drawing of the application of the present invention.
Figure 6:
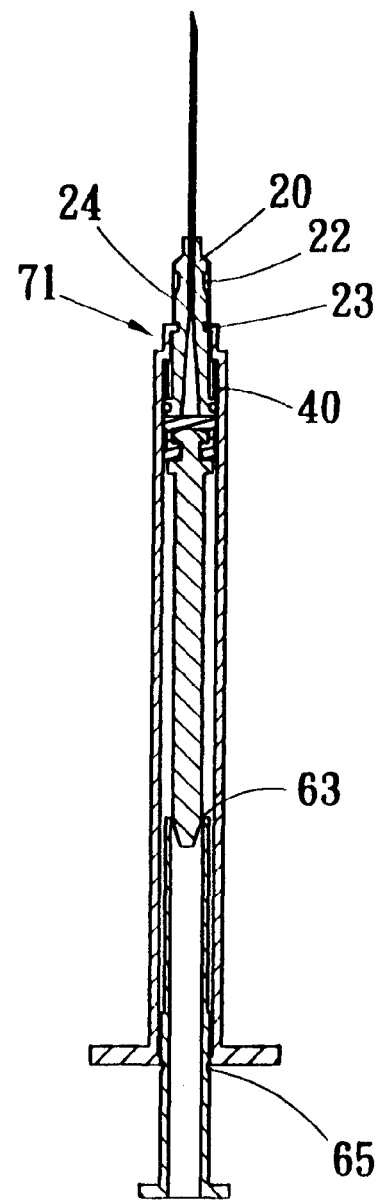
FIG. 6 is another drawing of the application of the present invention.
Figure 7:
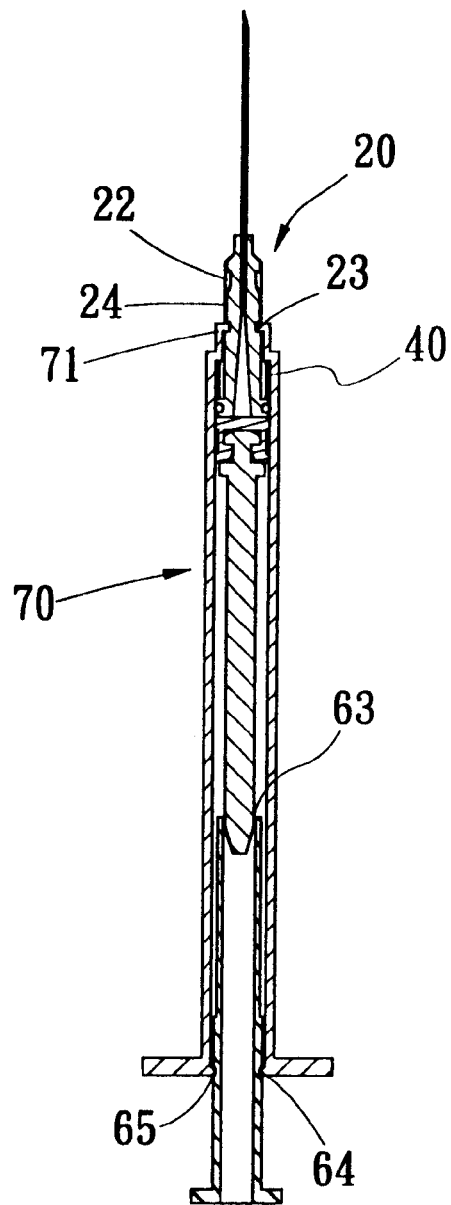
FIG. 7 is a drawing of the retracting action of the needle assembly of the present invention.
Figure 8:
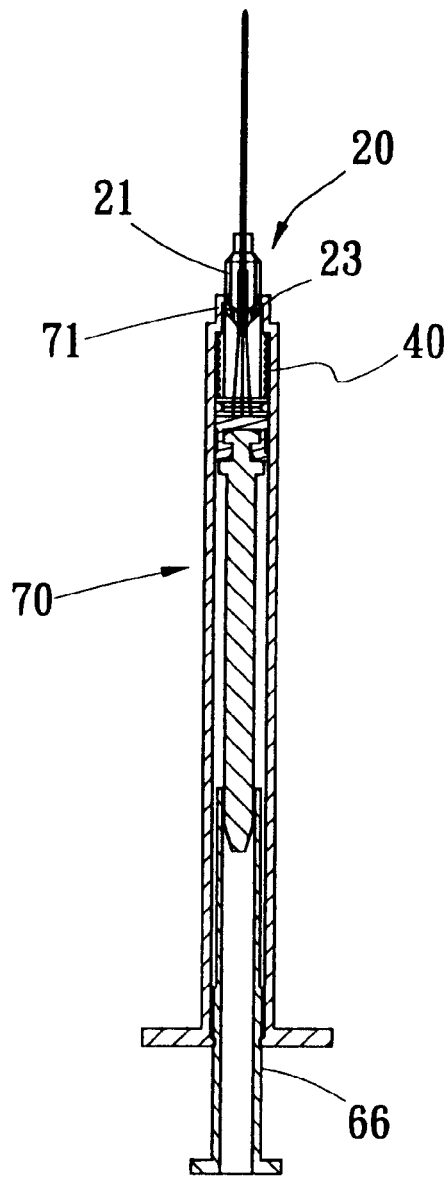
FIG. 8 is another drawing of the retracting action of the needle assembly of the present invention.
Figure 9:
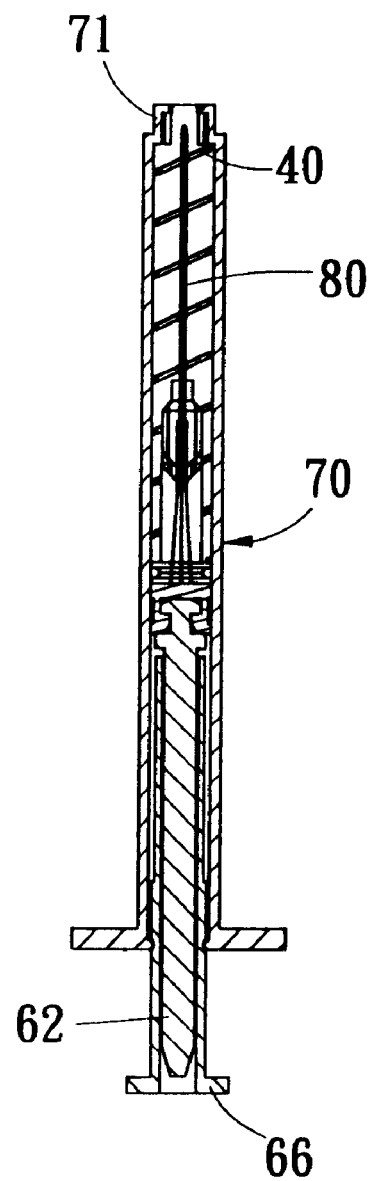
FIG. 9 is a drawing of the present invention in a destructive state.

As indicated in FIGS. 2 to 4C, the retaining hook (71) of the medicine barrel (70) of the present invention retains into the positioning slot (22) of the needle hub (20) to prevent the needle assembly from retracting inwardly due to the tension of the spring (40), as shown in FIG. 4A; one end of the long inwardly retracting rod (62) connects to one end of the hollow receiving rod (66) to form the breakable area (63) in an annular or annular block shape, as shown in FIG. 4B; the annular convex ring (73) controls and positions the bottom check ring (64) and the fastening annular groove (65), as shown in FIG. 4C; referring to FIGS. 5 and 6, the retracting spring (40) has a compressed space; the needle hub (20) is positioned and the convex ring (73) is clipped at the bottom check ring (64); the breakable inwardly retracting plunger (60) is forced inwardly; the retaining hook (71) moves along the proceeding slope (24) to reach the rotating slide passage (23); the retracting spring (40) reaches the limit; the breakable inwardly retracting plunger (60) breaks into two parts; the fastening annular groove (65) fitly clips to the convex ring (73); as shown in FIGS. 7 and 8, after the breakable inwardly retracting plunger (60) breaks into two parts, the retracting spring (40) starts to expand to drive the needle hub (20) to rotate and detach completely from the retaining hook (71) along the communicating slide passage (21) till the needle assembly retracts all the way into the inner barrel (72); FIG. 9 indicates the completely destructive state of the plunger (60) of the present invention.

To assemble the present invention of an automatically retractable safety syringe, the retracting spring (40) is first placed through the convex ring (73) of the inner barrel (72), then one end of the needle assembly penetrates through the retracting spring (40); the check plate (26) on the other end stops one end of the retracting spring (40); the positioning slot (22) of the needle hub (20) is positioned and clipped to the retaining hook (71); the area of the retracting spring (40) is in a halfway compressed state; then the breakable inwardly retracting plunger (60) and the plunger rubber gasket (50) retain with a retaining hole (51) via the rubber clip head (61); finally, two sets are assembled and the needle cap (10) is covered onto the retaining hook (71) to finish the assembly.

In accordance with the structure of the said automatically retractable safety syringe of the present invention, after the breakable inwardly retracting plunger assembled inside the medicine barrel is pushed all the way to the end, it is forced to break automatically into two parts for reducing it's length so as to provide enough space for the retracting spring to drive the needle assembly moving along the sliding passages for accomplishing the action of automatic retraction; therefore the present invention has less parts and thereby requires lower manufacturing cost; furthermore, the application is simple and safe; the present invention can be manufactured as an automatically retractable safety syringe in a smaller volume.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. An automatically retractable safety syringe to be adopted for injecting medicine comprising: a needle cannula, and a rotary and movable needle hub; an expandable retracting spring receiving a needle assembly in an interior space for storing kinetic energy; a breakable retracting plunger configured for breaking into a retracting rod and a hollow receiving tube; a plunger rubber gasket; a needle hub rubber gasket; a needle cap covering and guarding the needle assembly and clipping onto a retaining hook of a medicine barrel, such that, when the needle cap is not separated from the retaining hook of the medicine barrel, the retaining hook is not able to eject and the needle assembly cannot retract; an interior of the medicine barrel has a space for the needle assembly, the retracting spring, the breakable retracting plunger and the plunger rubber gasket; whereby, when the retracting spring area is over a halfway retracting state, the breakable retracting plunger drives the needle assembly and compresses the retracting spring; after the breakable retracting plunger breaks into two-parts the retracting rod and the hollow receiving tube, the retracting spring expands to move the needle assembly into the interior of the medicine barrel and the retracting rod into an interior of the hollow receiving tube for accomplishing the automatically retracting action.

2. The automatically retracting safety syringe according to claim 1, wherein one end of the needle hub receives the needle cannula fitly penetrating the center thereof for flowing the medicine; the circumference of the other end is disposed with an annular rubber gasket groove; a convex torus is disposed as a check plate at one end of a retracting spring; a plurality of concave positioning slits are disposed at two ends of the needle hub to connect a plurality of proceeding slopes tapered upwards, a plurality of rotating slide passages concaved inwardly and slanted for rotation as well as to connect a plurality of communicating slide passages concaved inwardly to form at least more than two U-shaped slide passages for the needle assembly to make retracting action.

3. An The automatically retracting safety syringe according to claim 1, wherein the retracting rod of the breakable retracting plunger has a rubber clip head on a first end to clip with the plunger rubber gasket, a second end of the retracting rod is connected to a first end of the hollow receiving tube with a breakable cutting edge area formed therebetween; a second end of the hollow receiving rod is disposed with a push grip; an annular bottom check ring is located on an outer periphery of the hollow receiving tube controlling the bottom position of the syringe; an annular fastening annular groove controls and fastens the breakable retracting plunger to break into two parts and rotates the needle assembly for completing inwardly retraction.

4. The automatically retracting safety syringe according to claim 1, wherein a first end of the cylindrical medicine barrel is disposed with a plurality of resilient retaining hooks pointing internally for engaging the needle hub; a second end is disposed with a handle lug; an aperture of the first end of cylindrical medicine barrel is smaller than an interior thereof to form a check ring for retaining the retracting spring; the second end of the cylindrical medicine barrel is disposed with an annular convex ring for controlling and positioning the bottom check ring and the fastening annular groove.

* * * * *